United States Patent
Helm et al.

(10) Patent No.: US 9,807,860 B2
(45) Date of Patent: *Oct. 31, 2017

(54) GATED IMAGE ACQUISITION AND PATIENT MODEL CONSTRUCTION

(75) Inventors: Patrick A. Helm, Littleton, MA (US); Shuanghe Shi, Southborough, MA (US)

(73) Assignee: Medtronic Navigation, Inc., Louisville, CO (US)

(*) Notice: Subject to any disclaimer, the term of this patent is extended or adjusted under 35 U.S.C. 154(b) by 101 days.

This patent is subject to a terminal disclaimer.

(21) Appl. No.: 12/908,189

(22) Filed: Oct. 20, 2010

(65) Prior Publication Data

US 2012/0099772 A1    Apr. 26, 2012

(51) Int. Cl.
| | | |
|---|---|---|
| *H05G 1/58* | (2006.01) | |
| *A61B 6/03* | (2006.01) | |
| *A61B 6/00* | (2006.01) | |

(52) U.S. Cl.
CPC .......... *H05G 1/58* (2013.01); *A61B 6/03* (2013.01); *A61B 6/481* (2013.01); *A61B 6/482* (2013.01); *A61B 6/487* (2013.01); *A61B 6/542* (2013.01)

(58) Field of Classification Search
CPC ......... A61B 6/481; A61B 6/482; A61B 6/032; A61B 6/504; A61B 5/7289; G06T 11/006; G06T 11/424; H05G 1/58; A61M 5/007; A61M 5/142
See application file for complete search history.

(56) References Cited

U.S. PATENT DOCUMENTS

| | | | |
|---|---|---|---|
| 4,477,923 A | 10/1984 | Baumann et al. | |
| 4,611,340 A | 9/1986 | Okazaki | |
| 4,672,651 A | 6/1987 | Horiba et al. | |
| 5,019,686 A | 5/1991 | Marantz | |
| 5,583,902 A | 12/1996 | Bae | |
| 5,689,629 A | 11/1997 | Lee | |
| 6,397,098 B1 | 5/2002 | Uber, III et al. | |
| 6,697,508 B2 | 2/2004 | Nelson | |
| 6,922,462 B2 | 7/2005 | Acharya et al. | |
| 7,386,089 B2 | 6/2008 | Endo et al. | |
| 7,460,635 B2 | 12/2008 | Fujimoto et al. | |
| 7,684,537 B2 | 3/2010 | Imai et al. | |
| 7,852,986 B2 | 12/2010 | Loef et al. | |

(Continued)

FOREIGN PATENT DOCUMENTS

| | | |
|---|---|---|
| CN | 101049244 A | 10/2007 |
| EP | 0486717 A1 | 5/1992 |

(Continued)

OTHER PUBLICATIONS

Montagnat, Johan, and Hervé Delingette. "Globally constrained deformable models for 3D object reconstruction." Signal Processing 71.2 (1998): 173-186. APA.*

(Continued)

*Primary Examiner* — Stephen R Koziol
*Assistant Examiner* — Raphael Schwartz
(74) *Attorney, Agent, or Firm* — Harness Dickey

(57) ABSTRACT

A method and system is disclosed for acquiring image data of a subject. The image data can be collected with an imaging system with at least two different power characteristics. A volumetric model of multiple phases can be reconstructed using dynamic or enhanced reconstruction techniques.

30 Claims, 3 Drawing Sheets

(56) References Cited

U.S. PATENT DOCUMENTS

| | | |
|---|---|---|
| 7,860,288 B2 | 12/2010 | Bernhardt et al. |
| 8,107,709 B2 | 1/2012 | Kawamura et al. |
| 9,769,912 B2 | 9/2017 | Helm et al. |
| 2003/0050750 A1 | 3/2003 | Kosling et al. |
| 2003/0152519 A1 | 8/2003 | Koenig et al. |
| 2003/0161435 A1 | 8/2003 | Ozaki |
| 2004/0101086 A1 | 5/2004 | Sabol et al. |
| 2004/0101088 A1* | 5/2004 | Sabol et al. ............... 378/4 |
| 2004/0116804 A1 | 6/2004 | Mostafavi |
| 2004/0170254 A1 | 9/2004 | Gregerson et al. |
| 2005/0080327 A1 | 4/2005 | Jenkins et al. |
| 2005/0084060 A1 | 4/2005 | Seppi et al. |
| 2005/0171426 A1* | 8/2005 | Rasche ............... 600/424 |
| 2005/0201509 A1* | 9/2005 | Mostafavi et al. ............... 378/8 |
| 2006/0052690 A1* | 3/2006 | Sirohey et al. ............... 600/420 |
| 2006/0251216 A1 | 11/2006 | Allred et al. |
| 2007/0009081 A1 | 1/2007 | Zhou et al. |
| 2007/0167738 A1 | 7/2007 | Timinger et al. |
| 2007/0189443 A1* | 8/2007 | Walter ............... A61B 6/032 378/4 |
| 2007/0238968 A1* | 10/2007 | Rappoport et al. ............... 600/407 |
| 2008/0123928 A1* | 5/2008 | Harer et al. ............... 382/131 |
| 2008/0206150 A1 | 8/2008 | Louie et al. |
| 2008/0212743 A1* | 9/2008 | Gregerson et al. ............... 378/197 |
| 2008/0232548 A1 | 9/2008 | Tanaka |
| 2008/0240355 A1 | 10/2008 | Ohishi |
| 2008/0242978 A1* | 10/2008 | Simon et al. ............... 600/426 |
| 2008/0285722 A1* | 11/2008 | Bertolina ............... 378/197 |
| 2008/0306381 A1 | 12/2008 | Feuerlein et al. |
| 2009/0010380 A1 | 1/2009 | Gotoh |
| 2009/0156927 A1* | 6/2009 | Schmidt ............... 600/420 |
| 2009/0232374 A1* | 9/2009 | Simon ............... 382/131 |
| 2010/0114064 A1 | 5/2010 | Kalafut et al. |
| 2010/0160776 A1 | 6/2010 | Goto et al. |
| 2010/0183117 A1 | 7/2010 | Tsumuraya et al. |
| 2010/0189210 A1 | 7/2010 | Nemoto |
| 2010/0202585 A1 | 8/2010 | Zaiki |
| 2010/0290690 A1 | 11/2010 | Hartmann et al. |
| 2010/0292570 A1 | 11/2010 | Tsukagoshi |
| 2011/0103542 A1 | 5/2011 | Allmendinger et al. |
| 2011/0135177 A1 | 6/2011 | Ohishi |
| 2012/0097178 A1 | 4/2012 | Helm |
| 2012/0099768 A1 | 4/2012 | Helm |

FOREIGN PATENT DOCUMENTS

| | | |
|---|---|---|
| EP | 1920717 A2 | 5/2008 |
| JP | 2000506398 A | 5/2000 |
| JP | 2001145619 A | 5/2001 |
| JP | 2004065975 A | 3/2004 |
| JP | 2005130929 A | 5/2005 |
| JP | 2005524419 A | 8/2005 |
| JP | 2005-536288 A | 12/2005 |
| JP | 2006296707 A | 11/2006 |
| JP | 2007021184 A | 2/2007 |
| JP | 2007143880 A | 6/2007 |
| JP | 2007519443 A | 7/2007 |
| JP | 2007319690 A | 12/2007 |
| JP | 2008096088 A | 4/2008 |
| JP | 2008154718 A | 7/2008 |
| JP | 2008154811 A | 7/2008 |
| JP | 2008253758 A | 10/2008 |
| JP | 2008264273 A | 11/2008 |
| JP | 2009056795 A | 3/2009 |
| JP | 2009077839 A | 4/2009 |
| JP | 2009119111 A | 6/2009 |
| JP | 2009131632 A | 6/2009 |
| JP | 2009-297584 A | 12/2009 |
| JP | 2009297517 A | 12/2009 |
| JP | 2010503145 A | 1/2010 |
| JP | 2010081977 A | 4/2010 |
| JP | 2010-516401 A | 5/2010 |
| JP | 2010142478 A | 7/2010 |
| JP | 2010167254 A | 8/2010 |
| WO | WO-2005076810 A2 | 8/2005 |
| WO | WO-2006034984 A1 | 4/2006 |
| WO | WO-2009123256 A1 | 10/2009 |
| WO | WO-2012054733 A2 | 4/2012 |
| WO | WO-2012054740 A1 | 4/2012 |
| WO | WO-2012103302 A2 | 8/2012 |

OTHER PUBLICATIONS

Yeh, Benjamin M., et al. "Dual energy and low kVp CT in the abdomen." AJR. American journal of roentgenology 193.1 (Jul. 2009): 47.*

Johnson, Thorsten RC, et al. "Material differentiation by dual energy CT: initial experience." European radiology 17.6 (2007): 1510-1517.*

"Medtronic O-Arm Multi-Dimensional Surgical Imaging System"; 2009.

International Search Report and Written Opinion dated Mar. 23, 2012 for PCT/US2011/057121 claiming benefit of U.S. Appl. No. 12/908,200, filed Oct. 20, 2010.

Invitation to Pay Additional Fees and Partial International Search dated Feb. 23, 2012 for PCT/US2011/057112 claiming benefit of U.S. Appl. No. 13/016,718, filed Jan. 28, 2011; and U.S. Appl. No. 12/908,189, filed Oct. 20, 2010.

Invitation to Pay Additional Fees and Partial International Search dated Feb. 7, 2012 for PCT/US2011/057121 claiming benefit of U.S. Appl. No. 12/908,200, filed Oct. 20, 2010.

International Search Report dated Jul. 3. 2012 for PCT/US2011/057112, claiming benefit of U.S. Appl. No. 13/016,718, filed Jan. 28, 2011 and U.S. Appl. No. 12/908,189, filed Oct. 20, 2010.

International Search Report dated Jul. 20, 2012 for PCT/US2012/022673 claiming benefit of U.S. Appl. No. 13/016,718, filed Jan. 28, 2011.

Gordon, et al, Algebraic Reconstruction Techniques (ART) for Three-dimensional Electron Microscopy and X-ray Photography, Dec. 1970, vol. 29, Issue 3, pp. 471-476.

International Preliminary Report on Patentability and Written Opinion dated Aug. 8, 2013 for PCT/US2012/022673 claiming benefit of U.S. Appl. No. 13/016,718, filed Jan. 28, 2011.

International Preliminary Report on Patentability and Written Opinion dated May 2, 2013 for PCT/US2011/057121 claiming benefit of U.S. Appl. No. 12/908,200, filed Oct. 20, 2010.

Second Chinese Office Action dated Jun. 17, 2015 for China Patent No. 201180061207.4.

Chinese Office Action dated Nov. 2, 2014 for China Patent Document No. 201180061207.4.

Japanese Office Action dated Nov. 4, 2014 for Japan Patent Document No. 2013-535094.

Second Chinese Office Action dated May 6, 2015 for China Patent Document No. 201180061219.7.

European Office Action dated Sep. 22, 2015 for European Patent Application No. 11777009.9.

Li "Dual-Energy CT with Fast-kVp Switching and Its Applications in Orthopedics" OMICS J Radiology, vol. 2, Issue 6, 8 pages, 2013.

European Office Action dated Mar. 10, 2016 for European Patent Application No. 11779032.9-1666.

Japanese Office Action dated Aug. 9, 2016 for Japanese Application No. 2015-017400 for PCT/US2011/057112 which claims benefit of U.S. Appl. No. 13/016,718, filed Jan. 28, 2011 (with English Translation).

European Summons to Attend Oral Proceedings dated Mar. 6, 2017 for European Patent Application No. 11777009.9 claiming benefit of PCT/US2011/057112 claiming benefit of U.S. Appl. No. 13/016,718, filed Jan. 28, 2011 and U.S. Appl. No. 12/908,189, filed Oct. 20, 2010.

Montagnat, J. et al., "Globally constrained deformable models for 3D object reconstruction," Signal Processing 71.2: 173-186 (1998).

Japanese Office Action dated Sep. 12, 2017 in corresponding Japanese Application No. 2016-239270.

* cited by examiner

GATED IMAGE ACQUISITION AND PATIENT MODEL CONSTRUCTION

FIELD

The present disclosure relates to imaging a subject, and particularly to determining and performing an optimal image data acquisition of the subject to model various physiological characteristic and anatomical features of the subject.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g. C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

According to various embodiments, a system to acquire image data of a patient with an imaging system using enhanced contrast imaging can include an imaging system having a first energy source with a first energy parameters and a second energy source with a second energy parameters. The imaging system can also include a pump operable to inject a contrast agent into the patient with an instruction. A controller can be in communication with both the imaging system and the pump. The imaging system can communicate with the pump through the controller regarding timing of the injection of a contrast agent into the patient and is further operable to acquire image data based upon the timing of the injection of the contrast agent and/or the clinical procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
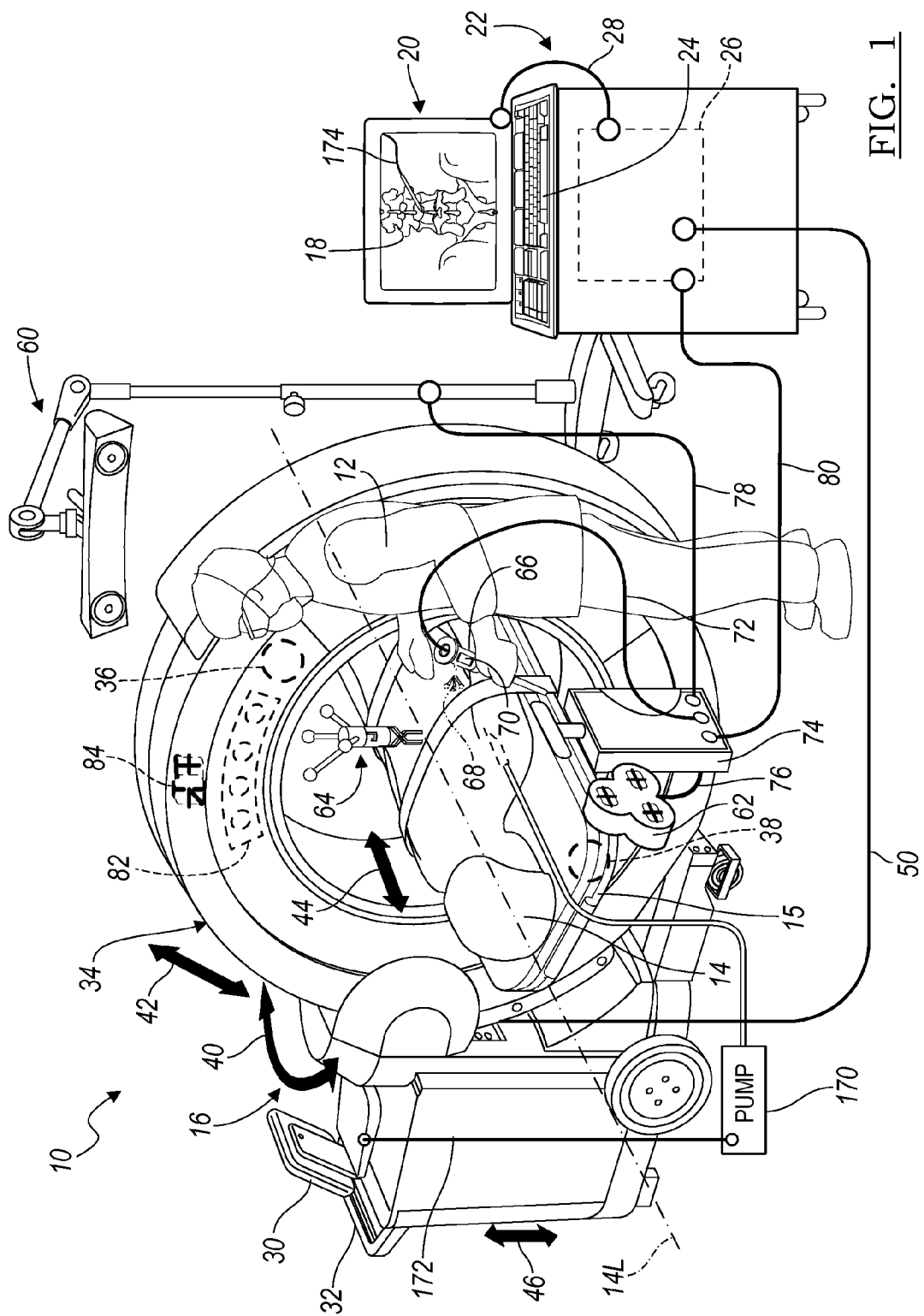
FIG. 1 is an environmental view of an imaging system in an operating theatre.

With reference to FIG. 1, in an operating theatre or operating room 10, a user, such as a surgeon 12, can perform a procedure on a patient 14. In performing the procedure, the user 12 can use an imaging system 16 to acquire image data of the patient 14 for performing a procedure. A model can be generated using the image data and displayed as image data 18 on a display device 20. The display device 20 can be part of a processor system 22 that includes an input device 24, such as a keyboard, and a processor 26 which can include one or more processors or microprocessors incorporated with the processing system 22. A connection 28 can be provided between the processor 26 and the display device 20 for data communication to allow driving the display device 20 to illustrate the image data 18.

The imaging system 16 can include an O-Arm® imaging system sold by Medtronic Navigation, Inc. having a place of business in Louisville, Colo., USA. The imaging system 16, including the O-Arm® imaging system, or other appropriate imaging systems in use during a selected procedure are also described in U.S. patent application Ser. No. 12/465,206 filed on May 13, 2009, incorporated herein by reference.

The O-Arm® imaging system 16 includes a mobile cart 30 that includes a control panel or system 32 and an imaging gantry 34 in which is positioned a source unit 36 and a detector 38. The mobile cart 30 can be moved from one operating theater to another and the gantry 34 can move relative to the cart 30, as discussed further herein. This allows the imaging system 16 to be mobile thus allowing it to be used in multiple locations and with multiple procedures without requiring a capital expenditure or space dedicated to a fixed imaging system.

The source unit 36 can emit x-rays through the patient 14 to be detected by the detector 38. As is understood by one skilled in the art, the x-rays emitted by the source 36 can be emitted in a cone and detected by the detector 38. The source/detector unit 36/38 is generally diametrically opposed within the gantry 34. The detector 38 can move in a 360° motion around the patient 14 within the gantry 34 with the source 36 remaining generally 180° opposed to the detector 38. Also, the gantry 34 can move isometrically relative to the subject 14, which can be placed on a patient support or table 15, generally in the direction of arrow 40 as illustrated herein. The gantry 34 can also tilt relative to the patient 14 illustrated by arrows 42, move longitudinally along the line 44 relative to a longitudinal axis 14L of the patient 14 and the cart 30, can move up and down generally along the line 46 relative to the cart 30 and transversely to the patient 14, to allow for positioning of the source/detector 36/38 relative to the patient 14. The O-Arm® imaging device 16 can be precisely controlled to move the source/detector 36/38 relative to the patient 14 to generate precise image data of the patient 14. The imaging device 16 can be connected with the processor 26 via connection 50 which can include a wired or wireless connection or physical media transfer from the imaging system 16 to the processor 26. Thus, image data collected with the imaging system 16 can be transferred to the processing system 22 for navigation, display, reconstruction, etc.

Briefly, according to various embodiments, the imaging system 16 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. The navigated space or navigational domain relative to the patient 14 can be registered to the image data 18 to allow registration of a navigation space defined within the navigational domain and an image space defined by the image data 18. A patient tracker or dynamic reference frame 64 can be connected to the patient 14 to allow for a dynamic registration and maintenance of registration of the patient 14 to the image data 18.

A patient tracking device or dynamic registration device 64 and an instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74 as can the electromagnetic localizer 62 with communication line 76 and/or the optical localizer 60 with communication line 78. Using the communication lines 74, 78 respectively, the probe interface 74 can then communicate with the processor 26 with a communication line 80. It will be understood that any of the communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 being any appropriate instrument, such as a ventricular or vascular stent, spinal implant, neurological stent or stimulator, ablation device, or the like. The instrument 66 can be an interventional instrument or can include or be an implantable device. Tracking the instrument 66 allows for viewing the instrument's 66 location relative to the patient 14 with use of the registered image data 18 without direct viewing of the instrument 66 within the patient 14.

Further, the gantry 34 can include an optical tracking device 82 or an electromagnetic tracking device 84 to be tracked with a respective optical localizer 60 or electromagnetic localizer 62. Accordingly, the imaging device 16 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206.

Figure 2:
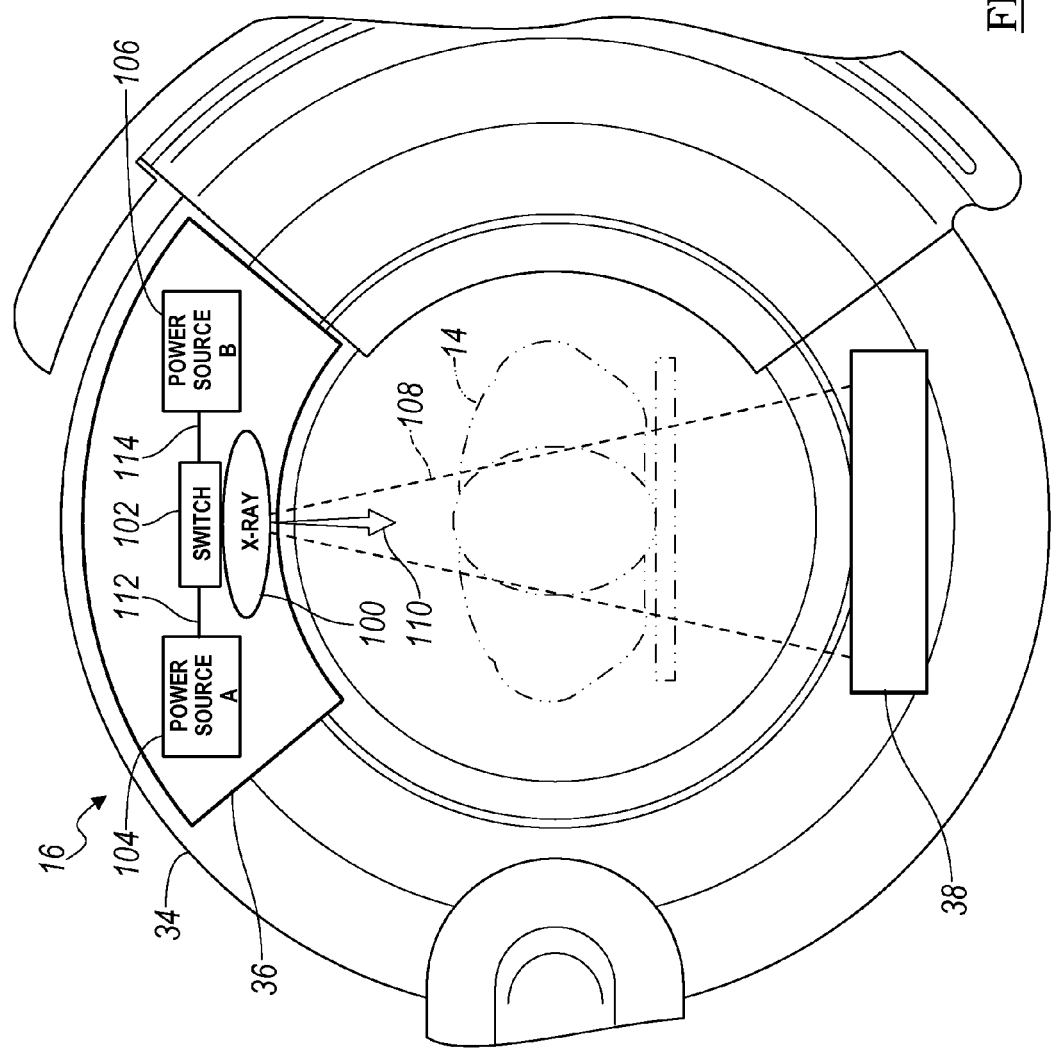
FIG. 2 is a detail view of an imaging system with a dual energy source system.

With reference to FIG. 2, according to various embodiments, the source 36 can include a single x-ray tube 100 that can be connected to a switch 102 that can interconnect a power source A 104 and a power source B 106 with the x-ray tube 100. X-rays can be emitted generally in a cone shape 108 towards the detector 38 and generally in the direction of the vector 110. The switch 102 can switch between the power source A 104 and the power source B 106 to power the x-ray tube 100 at different voltages and amperages to emit x-rays at different energies generally in the direction of the vector 110 towards the detector 38. It will be understood, however, that the switch 102 can be connected to a single power source that is able to provide power at different voltages and amperages rather than the 102 switch that connects to two different power sources A 104, and B 106. Also, the switch 102 can be a switch that operates to switch a single power source between different voltages and amperages. The patient 14 can be positioned within the x-ray cone 108 to allow for acquiring image data of the patient 14 based upon the emission of x-rays in the direction of vector 110 towards the detector 38.

The two power sources A and B 104, 106 can be provided within the source housing 36 or can be separate from the source 36 and simply be connected with the switch 102 via appropriate electric connections such as a first cable or wire 112 and a second cable or wire 114. The switch 102 can switch between the power source A 104 and the power source B 106 at an appropriate rate to allow for emission of x-rays at two different energies through the patient 14 for various imaging procedures, as discussed further herein. The differing energies can be used for material separation and/or material enhanced reconstruction or imaging of the patient 14.

The switching rate of the switch 102 can include about 1 millisecond to about 1 second, further including about 10 ms to 500 ms, and further including about 50 ms. Further, the power source A 104 and the power source B 106 can include different power characteristics, including different voltages and different amperages, based upon selected contrast enhancement requirements. For example, as discussed further herein, it can be selected to allow for contrast enhancement between soft tissue (e.g. muscle or vasculature) and hard tissue (e.g. bone) in the patient 14 or between a contrast agent injected in the patient 14 and an area without a contrast agent injected in the patient 14.

As an example, the power source A 104 can have a voltage of about 75 kV and can have an amperage of about 50 mA, which can differ from the power source B which can have a voltage of 125 kV and 20 mA. The selected voltages and amperages can then be switched with the switch 102 to power the x-ray tube 100 to emit the appropriate x-rays generally in the direction of the vector 110 through the patient 14 to the detector 38. It will be understood that the range of voltages can be about 40 kV to about 80 kV and the amperages can be about 10 mA to about 500 mA. Generally, the power characteristics differences between the first power source A 104 and the second power source B 106 can be about 40 kV to about 60 kV and about 20 mA to about 150 mA.

The dual power sources allow for dual energy x-rays to be emitted by the x-ray tube 100. As discussed above, the two or dual energy x-rays can allow for enhanced and/or dynamic contrast reconstruction of models of the subject 14 based upon the image data acquired of the patient 14. Generally an iterative or algebraic process can be used to reconstruct the model of at least a portion of the patient 14 based upon the acquired image data. It will be understood, however, that any appropriate number of power sources or switching possibilities can be provided. Two is included in the subject disclosure merely for clarity of the current discussion.

The power sources can power the x-ray tube 100 to generate two dimension (2D) x-ray projections of the patient 14, selected portion of the patient 14, or any area, region or volume of interest. The 2D x-ray projections can be reconstructed, as discussed herein, to generate and/or display three-dimensional (3D) volumetric models of the patient 14, selected portion of the patient 14, or any area, region or volume of interest. As discussed herein, the 2D x-ray projections can be image data acquired with the imaging system 16, while the 3D volumetric models can be generated or model image data.

Appropriate algebraic techniques include Expectation maximization (EM), Ordered Subsets EM (OS-EM), Simultaneous Algebraic Reconstruction Technique (SART) and Total Variation Minimization (TVM), as generally understood by those skilled in the art. The application to performing a 3D volumetric reconstruction based on the 2D projections allows for efficient and complete volumetric reconstruction. Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. The theoretical model can be associated with theoretical image data to construct the theoretical model. In this way, the model or the image data 18 can be built based upon image data acquired of the patient 14 with the imaging device 16.

The 2D projection image data can be acquired by substantially annular or 360° orientation movement of the source/detector 36/38 around the patient 14 due to positioning of the source/detector 36/38 moving around the patient 14 in the optimal movement. Also, due to movements of the gantry 34, the detector need never move in a pure circle, but rather can move in a spiral helix, or other rotary movement about or relative to the patient 14. Also, the path can be substantially non-symmetrical and/or non-linear based on movements of the imaging system 16, including the gantry 34 and the detector 38 together. In other words, the path need not be continuous in that the detector 38 and the gantry 34 can stop, move back the direction from which it just came (e.g. oscillate), etc. in following the optimal path. Thus, the detector 38 need never travel a full 360° around the patient 14 as the gantry 34 may tilt or otherwise move and the detector 38 may stop and move back in the direction it has already passed.

In acquiring image data at the detector 38, the dual energy x-rays generally interact with a tissue and/or a contrast agent in the patient 14 differently based upon the characteristics of the tissue or the contrast agent in the patient 14 and the energies of the two x-rays emitted by the x-ray tube 100. For example, the soft tissue of the patient 14 can absorb or scatter x-rays having an energy produced by the power source A 104 differently than the x-rays having energy produced by the power source B 106. Similarly, a contrast agent, such as iodine, can absorb or scatter the x-rays generated by the power source A 104 differently from those generated by the power source B 106. Switching between the power source A 104 and the power source B 106 can allow for determination of different types of material properties (e.g. hard or soft anatomy), or contrast agent, implants, etc. within the patient 14. By switching between the two power sources 104, 106 and knowing the time when the power source A 104 is used to generate the x-rays as opposed to the power source B 106 to generate the x-rays the information detected at the detector 38 can be used to identify or segregate the different types of anatomy or contrast agent being imaged.

A timer can be used to determine the time when the first power source A 104 is being used and when the second power source B 106 is being used. This can allow the images to be indexed and separated for generating different models of the patient 14. Also, as discussed herein, the timer, which can be a separate system or included with the imaging system 16 or the processor system 26, can be used to index image data generated with the contrast agent injected into the patient 14.

Figure 3B:
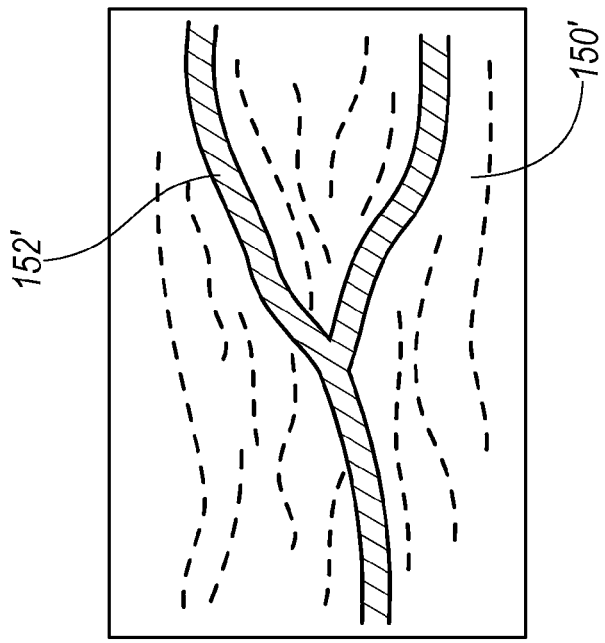
FIG. 3B is a schematic representation of a contrast enhanced image data.
Figure 3A:
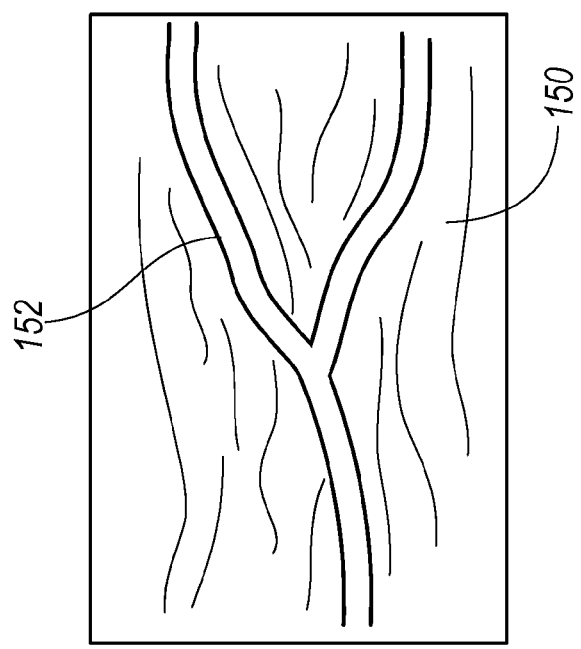
FIG. 3A is a schematic representation of non-contrast enhanced image data.

With reference to FIG. 3A, image data acquired when powering the x-ray tube 100 with the power source 104 is schematically illustrated. As illustrated in FIG. 3A, the image data can include image data of soft tissue, such as surrounding tissues 150 that surround a vasculature 152. As illustrated in FIG. 3A, the power source A 104 can generate x-rays of the x-ray tube 100 that provide substantially little contrast between the vasculature 152 and the surrounding tissue 150, even if a contrast agent is present in the vasculature agent 152, such as iodine. With reference to FIG. 3B, however, the second power source B 106 can be used to generate second energy x-rays to acquire image data that illustrates the surrounding tissue 150' relative to the vasculature 152'. This can be further enhanced with a contrast agent that can be injected into the patient 14. As is understood in the art, the two power levels have different attenuations based on the materials in the patient 14. This differing attenuation can be used to differentiate materials, e.g. vasculature 152 and the surrounding tissue 150, in the patient 14.

With the acquisition of the image data illustrated in FIG. 3A and FIG. 3B, a reconstruction can be made to clearly identify the vasculature 152 of the patient 14 separate from the surrounding tissue 150 of the patient 14. The dual energy system can be used to reconstruct a model of the vasculature 152 of the patient 14 to discriminate the vasculature 152 from the surrounding tissue 150 of the patient 14. In identifying the vasculature 152, the imaging system 16, including the O-Arm® imaging system, can be used to efficiently image the vasculature 152 of the patient 14 in the operating theatre 10 during a procedure, such as a valve replacement procedure, a stent procedure, an inclusion ablation procedure, or an angioplasty procedure.

At least because the x-ray tube 100 is in a moveable imaging system, such as the imaging system 16, it can be moved relative to the patient 14. Thus, the x-ray tube 100 may move relative to the patient 14 while the energy for the x-ray tube 100 is being switched between the first power source 104 and the second power source 106. Accordingly, an image acquired with the first power source 104 may not be at the same pose or position relative to the patient 14 as the second power source 106. If a model is desired or selected to be formed of a single location in the patient 14, however, various interpolation techniques can be used to generate the model based on the amount of movement of the x-ray tube 100 between when the projection with the first power source 104 and the projection with the second power source 106 was acquired.

The dual energy of the x-rays emitted by the x-ray tube 100 due to the two power sources 104, 106 can allow for substantially efficient and enhanced contrast discrimination determination between the vasculature 152 and the musculature 150 of the patient 14. Moreover, the switching by a switch 102 between the power source A 104 and the power source B 106 allows for an efficient construction of the source 36 where the single x-ray tube 100 can allow for the generation of x-rays at two different energies to allow for enhanced or dynamic contrast modeling of the patient 14, such as modeling the vasculature of the patient 14 including a contrast agent therein.

The patient 14 can also be imaged with the injected contrast agent by gating the acquisition of the image data of the patient 14 based upon the injection of the contrast agent. According to various embodiments, a contrast agent, such as iodine, can be injected into the patient 14 to provide additional contrast in the image data acquired of the patient 14 with the imaging system 16. During the image acquisition, however, the contrast agent flows through the vasculature of the patient 14 from an artery phase to a venous phase. For example, the contrast agent can be injected into the patient 14 into an artery where the contrast agent can flow through the vasculature of the patient 14 to the heart, through the heart, to the lungs through the venous system, back through the heart, and out into the arterial portion of the vasculature of the patient 14.

When acquiring image data of the patient 14 to identify or reconstruct the vasculature of the patient 14, knowing the timing of when image data is acquired relative to the timing of the injection of the contrast agent can allow for a reconstruction of the various phases based on the known movement of the contrast agent through structures of the patient 14. In other words, it is generally understood that the contrast agent will flow through the patient 14 as described above at a known or generally known rate. As illustrated in FIG. 3B, the dual energy x-rays, generated with the x-ray tube 100 based upon the power source A 104 and the power source B 106, can be used to generate image data of any portion of the vasculature of the patient 14.

The acquisition of the image data, therefore, can be gated relative to the injection of the contrast agent into the patient 14. For example, the controls 32 of the imaging system 16 can be associated or communicate with a control of a pump 170 (illustrated in FIG. 1) through a communication line 172 (illustrated in FIG. 1) that pumps or injects the contrast agent into the patient 14. The communication 172 between the pump 170 and the imaging device control 32 can be any appropriate communication such as a wired, wireless, or other data communication system. Also, the control 170 for the pump can be incorporated into the controls 32 of the imaging system 16 or the processor system 26.

According to various embodiments, the control system 32 for the imaging system 16 can control the pump 170 to initiate injection of the contrast agent into the patient 14. The imaging system 16 can then acquire image data of the patient 14 over a set period of time to identify the difference between an arterial phase and a venous phase in the patient 14. For example, the imaging system can control the pump 170 to inject the contrast agent and then acquire image data for approximately 10 seconds to approximately 20 second including approximately 13 seconds. The imaging system 16 can identify or separate a first portion of the image data, such as about 5 second to about 7 seconds, including about 6 seconds as an arterial phase and a second phase of the image data, such as image data acquired after about 6 second to about 8 seconds, including about 7 seconds as a venous phase. In other words, the control system 32, or other appropriate processor system, can index the image data to determine when the image data was acquired. Also, it will be understood that the image data can be acquired at the two energies. Thus, the controls 32 or other appropriate processing system (e.g. a timer) can index the image data based on which of the two power sources 104, 106 were used to power the x-ray tube 100.

After the acquisition of the image data and determining a segregation of time of image data acquisition, a reconstruction of the vasculature of the patient 14 can then be made to illustrate or identify or reconstruct an arterial phase of the patient 14 and separately a venous phase of the patient 14. Accordingly, the imaging system 16 controlled with the controller 32 can be used to acquire image data of both a venous phase and an arterial phase of the patient 14 in a single image data acquisition sweep or period. In other words, the phase determination and reconstruction of an arterial phase and a venous phase of the vasculature of the patient 14 can be based on a single image data acquisition phase of the patient 14. Again, this can minimize or limit the exposure of the patient 14 and operating room staff to x-rays emitted from the x-ray tube 100 by requiring only a single image data acquisition phase. It will be understood, however, that a plurality of image data acquisition phases can be acquired of the patient 14.

The control system 32 of the imaging system 16 can be used to gate acquisition of the image data in addition to or with timing of the pump 170. For example, it can be selected to acquire image data of the vasculature of the patient 14 during diastole of the heart. During diastole of the heart of the patient 14, the heart generally does not move and blood in the vasculature is also relatively still. Accordingly, the image data can be acquired of the patient 14 by gating the acquisition of the image data relative to the heart movement of the patient 14. The generation of the x-rays with the x-ray tube 100 can be switched with the switch 102 to allow for time emission of x-rays from the x-ray tube 100.

The image data can be acquired by emitting x-rays from the x-ray tube 100 substantially sequentially such that at a selected period of time no x-rays are emitted by the x-ray tube 100 and at a different or second selected time x-rays are emitted from the x-ray tube 100. The x-rays emitted from one period to another can be at either of the two energies allowed by the power source A 104 or the power source B 106. Accordingly, at various times no x-rays can be emitted from the x-ray tube 100, but at other times x-rays can be emitted from the x-ray tube at a selected energy.

In being able to control the image system to emit or not emit x-rays image data acquisition can be gated relative to a physiological event of the patient 14. It will be further understood that gating of the image acquisition can be based upon respiration of the patient 14, physical movement of the patient 14, and other physiological events. The control system 32 can also be used to index the image data regarding whether acquired during a physiological event or not. The physiological event can be determined with an appropriate system, such as an electrocardiogram, or based on a regular rate of image acquisition (e.g. diastole occurs about 2 seconds in the patient 14).

Also, due to gating of the imaging system 16 relative to the patient 14, the control system 32 can also be used to control the imaging system 16 to control the speed of the detector 38 relative to the patient 14. As discussed above, the detector 38 of the imaging system can translate within the gantry 34 of the imaging system 16 to acquire image data of the patient 14. Further as discussed above, image data can be selected to be acquired of the patient 14 during only selected physiological events, such as diastole of the heart. To generate or form a three-dimensional model of at least a portion of the patient 14, it can be selected to have separation of a selected amount between acquisitions of images of the patient 14.

The detector 38 can be moved at a selected speed and change speeds to ensure appropriate separation of the images during the selected physiological events. The detector 38 can move at a first speed during a first physiological event such as systole of the heart, and at a second speed, such as a greater speed, during diastole of the heart to ensure appropriate separation of acquisition of images of the patient 14 during the selected physiological event.

In generating the 3D volumetric reconstruction to form the model, as discussed above, the model may be multi-phase to illustrate a selected portion of the patient to illustrate a first phase of physiological action and anatomical location and a second phase of physiological action and anatomical location. Thus, the model, or more than one model, can be used to illustrate a first phase (e.g. an arterial phase) and a second phase (e.g. venous phase) of the patient 14. Also, due to gating and movement of the detector 38 a first position of the detector 38 during image data acquisition and a second position of the detector 38 during image data acquisition can be used in the generating the first model and generating the second model to illustrate more than one phase of a physiological action of the patient 14. Additionally, the anatomy of the patient 14 and the physiology of the patient 14 can be used to form the 3D reconstruction. For example, the configuration of a bone of the patient 14 or a phase of a heart beat of the patient 14 can be used as a priori knowledge to assist in model reconstruction.

Also, the controller 32 of the imaging system 16 can be used to "rewind" or move the detector 38 back over the same path just traversed by the detector 38. Even while moving in a selected single path or direction, the detector 38 can be stopped and started, for example for gating or acquiring additional image data (e.g. x-ray projections) at a selected location. Accordingly, the controller 32 can control the imaging system 16 to achieve a selected separation of images relative to the patient 14 for reconstruction of an appropriate or selected model of the patient 14 based upon the required image data.

The reconstruction based on the image data or the raw image data can be used to perform a procedure on the patient 14. As discussed above selected navigation or tracking systems can be associated with the imaging system 16. Accordingly, the patient 14 can be registered to the image data and a navigation procedure can be performed. The navigated procedure can include placement of a stent in the patient's 14 heart, brain, or other vasculature, ablation procedures, angioplasty, implant placement or bone resection. Navigation can include tracking or determining automatically a location of an instrument positioned in a navigation field relative to a selected reference frame, such as in patient space, during a surgical procedure. The location of the instrument 66 can be illustrated on the display device 20 with an icon 174 that can be superimposed on the image data or the reconstructed model or image data 18.

It will also be understood that the image data and/or model can be used to plan or confirm a result of a procedure without requiring or using navigation and tracking. The image data can be acquired to assist in a procedure, such as an implant placement. Also, the image data can be used to identify blockages in the vasculature of the patient 14, such as with the contrast agent. Thus, navigation and tracking are not required to use the image data in a procedure.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of acquiring image data of a patient with an imaging system using enhanced contrast imaging, comprising:

controlling with a controller of an imaging system a selected path, including a plurality of selected movements, of a single x-ray source tube during a passage of time after the start time to acquire image data of a first selected portion of the patient, wherein the selected path includes at least one of a spiral path, a helical path, a non-annular path, and a non-360° path around the patient;

powering the single x-ray source tube to emit x-rays at a first power with a first power source to acquire a first image data at a first position along the path relative to the patient and having a first attenuation, including x-ray absorption or x-ray scatter, in tissue within the patient;

powering the single x-ray source tube to emit x-rays at a second power different from the first power with a second power source to acquire a second image data at a second position along the path relative to the patient and having a second attenuation, including x-ray absorption or x-ray scatter, in tissue different than the first attenuation within the patient; and acquiring the first image data and the second image data of the first selected portion of the patient at both the first power and the second power; and reconstructing a model of the first selected portion of the patient including the first image data with the first attenuation, including a first x-ray absorption or x-ray scatter in the tissue, and the second image data with the second attenuation, including a second x-ray absorption or x-ray scatter in the tissue and based on a known timing of acquiring the first image data and the second image data;

wherein reconstructing the model of the selected portion of the patient includes:

constructing the multi-phase three-dimensional model to illustrate (i) a first phase including a venous phase of a physiological action at a first anatomical location and (ii) a second phase including an arterial phase of the physiological action at a second anatomical location, and iteratively changing a pre-formed theoretical image data projection based on the patient until the pre-formed theoretical image data projection matches the acquired image data of the patient to form an appropriately altered reconstruction model;

wherein the first power is selected to have a first voltage of about 40 kV to about 180 kV and a first amperage of about 10 mA to about 500 mA;

wherein the second power is selected to have a second voltage that is about 40 kV to about 60 kV different than the first voltage and a second amperage that is about 20 mA to about 150 mA different than the first amperage.

2. The method of claim 1, further comprising:
moving the single x-ray source tube to the first selected position along the path relative to the patient in a selected operating theater.

3. The method of claim 2, further comprising:
switching powering the single x-ray source tube between the first power source and the second power source.

4. The method of claim 3, wherein reconstructing the single model further includes:
executing instructions with a processor to determine a difference between the first image data acquired at the first power and the second image data acquired at the second power;
differentiating a vasculature from a surrounding soft tissue based on the first image data acquired at the first power and the second image data acquired at the second power;
wherein reconstructing the model includes executing instructions with the processor to reconstruct a model of the selected portion of the patient including illustrating a first region in the selected portion and a second region in the selected portion based on the determined difference in the first and second image data, the anatomy of the patient being imaged, the selected portion of the patient, anatomical region of interest, timing or rhythm of a physiology of the patient.

5. The method of claim 4, further comprising:
displaying the reconstructed model;
wherein executing instructions with the processor to reconstruct the model of the selected portion of the patient includes reconstructing a multi-phase three-dimensional model of the selected portion of the patient.

6. The method of claim 5, wherein the second phase of the physiological action at the second anatomical location is different than the first phase of the physiological action at the first anatomical location.

7. A method of acquiring image data of a patient with an imaging system, comprising:
moving and controlling a single x-ray source tube and an associated detector along a determined path relative to the patient to acquire x-ray image data to generate a first model of the patient and a second model of the patient;
moving a housing including the single x-ray source tube and the associated detector into a selected operating theater and to a position relative to the patient;
moving the single x-ray source tube and the associated detector to a first selected position relative to the patient based on the determined path;
after moving the single x-ray source tube and the associated detector to the first selected position relative to the patient based on the determined path,
powering the single x-ray source tube at a first power to emit x-rays in a first cone of x-rays through the patient,
powering the single x-ray source tube at a second power different from the first power to emit x-rays in a second cone of x-rays through the patient, and
acquiring a first x-ray image data at both the first power and the second power for a first period of time at the first selected position relative to the patient;
after the first period of time,
powering the single x-ray source tube at the first power to emit x-rays in a third cone of x-rays through the patient,
powering the single x-ray source tube at the second power different from the first power to emit x-rays in a fourth cone of x-rays through the patient, and
acquiring a second x-ray image data at both the first power and the second power for a second period of time after the first period of time and at the first selected position relative to the patient;
after acquiring the first image data and the second image data,
differentiating between a vasculature and a surrounding tissue including the acquired first x-ray image data and the acquired second x-ray image data and based a first attenuation, including x-ray absorption or x-ray scatter, caused by the vasculature different than a second attenuation caused by the surrounding tissue within the patient;
reconstructing a first model of a venous structure at a first location of the patient based on using the first image data at the first selected position of the single x-ray source tube and the associated detector relative to the patient, at least by the differentiating the vasculature from the surrounding tissue and by iteratively changing a first pre-formed theoretical image data projection based on the patient until the first pre-formed theoretical image data projection matches the acquired image data of the patient to form a first appropriately altered reconstruction model, and
reconstructing a second model of an arterial structure at the first location of the patient based on using the second image data at the first selected position of the single x-ray source tube and the associated detector relative to the patient, at least by the differentiating the vasculature from the surrounding tissue and by iteratively changing a second pre-formed theoretical image data projection based on the patient until the second pre-formed theoretical image data projection matches the acquired image data of the patient to form a second appropriately altered reconstruction model; and
operating a tracking system to track the imaging system and track the patient during at least acquiring the first x-ray image data and acquiring the second x-ray image data;
wherein the first power is selected to have a first voltage of about 40 kV to about 180 kV and a first amperage of about 10 mA to about 500 mA;
wherein the second power is selected to have a second voltage that is about 40 kV to about 60 kV different than the first voltage and a second amperage that is about 20 mA to about 150 mA than the first amperage.

8. The method of claim 7, further comprising:
moving the single x-ray source tube and the associated detector from a first selected position relative to the patient after the first period of time to a second selected position before the second period of time;
wherein the first image data is collected at a first position and the second image data is collected at a different second position.

9. The method of claim 8, wherein the first position and the second position are used in the generating the first model and generating the second model to illustrate more than one phase of a physiological action of the patient.

10. The method of claim 6, wherein controlling with the controller the path includes controlling forward movement, rewind movement, starting of movement, and stopping of movement to acquire image data of the patient upon which the reconstructed multi-phase model is based and wherein reconstructing the multi-phase model of the selected portion of the patient includes interpolating accounting for a difference in position of the x-ray source tube between the first image data and the second image data.

11. The method of claim 9, further comprising:
displaying the first model separate from the second model with a display device.

12. The method of claim 7, further comprising:
navigating a surgical procedure at least by superimposing an icon of a device over the appropriately altered reconstruction model.

13. The method of claim 1, wherein the selected path includes at least one of a non-symmetrical path, a non-linear path, a non-continuous motion of the single x-ray source tube, an oscillating path, a stop and move back in the direction the single x-ray source tube has already passed path, or combinations thereof.

14. The method of claim 1, wherein the selected path includes at least a rotational movement around the patient and a straight path along an axis of the patient.

15. The method of claim 1, wherein the pre-formed theoretical image data is based on at least one of a configuration of a bone of the patient or a phase of a heartbeat of the patient.

16. The method of claim 5, wherein reconstructing a multi-phase model of the selected portion of the patient includes constructing the multi-phase model to illustrate the venous phase of a vasculature and the arterial phase of a vasculature, wherein the venous phase and the arterial phase are separate;
wherein the multi-phase model is based on indexed image data, including:
controlling with a controller gating the acquiring the first image data and the second image data based on a physiological event of the patient.

17. The method of claim 7, wherein the determined path includes a linear path portion and a non-linear path portion;
wherein the determined path further includes at least a rewind path wherein the single x-ray source tube and the associated detector stop and move back along the determined path in both the linear path portion and the non-linear path.

18. The method of claim 17, wherein the non-linear path portion includes at least a rotational movement around the patient and the linear path portion includes a straight path along an axis of the patient.

19. The method of claim 7, further comprising:
displaying with a display device a multi-phase model as a 3D volumetric reconstruction of the reconstructed first model of the venous structure and the reconstructed second model of the arterial structure.

20. The method of claim 7, further comprising:
based on tracking the imaging system and the patient, registering the generated first model with the patient and the generated second model with the patient.

21. A method of acquiring image data of a patient with an imaging system using imaging, comprising:
controlling with a controller of an imaging system a selected path, including a plurality of selected movements, of a x-ray source tube during a passage of time after the start time to acquire image data of a first selected portion of the patient;
powering the x-ray source tube to emit x-rays at a first power with a first power source to acquire a first image data at a first position along the path relative to the patient and having a first attenuation, including x-ray absorption or x-ray scatter, caused by a first tissue within the patient;
powering the x-ray source tube to emit x-rays at a second power different from the first power with a second power source to acquire a second image data at a second position along the path relative to the patient and having a second attenuation, including x-ray absorption or x-ray scatter, caused by a second tissue different than the first attenuation caused by the first tissue within the patient; and
acquiring the first image data and the second image data of the first selected portion of the patient at both the first power and the second power; and
reconstructing a single model of the first selected portion of the patient including the first image data with the first attenuation, including a first x-ray absorption or x-ray scatter caused by the first tissue, and the second image data with the second attenuation, including a second x-ray absorption or x-ray scatter caused by the second tissue;
wherein the first tissue is different than the second tissue;
wherein reconstructing the single model includes:
constructing a multi-phase three-dimensional model of the selected portion of the patient to illustrate (i) a first phase including a venous phase of a physiological action at a first anatomical location and (ii) a second phase including an arterial phase of the physiological action at a second anatomical location, and
iteratively changing a pre-formed theoretical image data projection of the patient until the pre-formed theoretical image data projection matches the acquired image data of the patient to form an appropriately altered reconstruction model;
wherein the first power is selected to have a first voltage of about 40 kV to about 180 kV and a first amperage of about 10 mA to about 500 mA;
wherein the second power is selected to have a second voltage that is about 40 kV to about 60 kV different than the first voltage and a second amperage that is about 20 mA to about 150 mA different than the first amperage.

22. The method of claim 21, further comprising:
moving the x-ray source tube to the first selected position along the path relative to the patient in a selected operating theater;
wherein the x-ray source tube is a single x-ray source tube powered by both the first power source and the second power source.

23. The method of claim 22, further comprising:
switching powering the single x-ray source tube between the first power source and the second power source.

24. The method of claim 23, wherein reconstructing the single model further includes:
executing instructions with a processor to determine a difference between the first image data acquired at the first power and the second image data acquired at the second power;
differentiating a vasculature from a surrounding soft tissue based on the first image data acquired at the first power and the second image data acquired at the second power;
wherein reconstructing the single model includes executing instructions with the processor to reconstruct a model of the selected portion of the patient including illustrating a first region in the selected portion and a second region in the selected portion based on the determined difference in the first and second image data, the anatomy of the patient being imaged, the selected portion of the patient, anatomical region of interest, timing or rhythm of a physiology of the patient.

25. The method of claim 24, further comprising:
displaying the reconstructed single model;
wherein executing instructions with the processor to reconstruct the model of the selected portion of the patient includes reconstructing a multi-phase three-dimensional model of the selected portion of the patient.

26. The method of claim 25, wherein the second phase of the physiological action at the second anatomical location is different than the first phase of the physiological action at the first anatomical location.

27. The method of claim 21, wherein the first tissue is soft tissue and the second tissue is hard tissue.

28. The method of claim 21, wherein the first tissue is a vasculature.

29. The method of claim 21, wherein the first position along the path is different than the second position along the path.

30. The method of claim 21, further comprising:
executing instructions with a processor to construct the multi-phase three-dimensional model of the selected portion of the patient.

* * * * *